United States Patent
Kawasaki et al.

(10) Patent No.: US 6,482,251 B1
(45) Date of Patent: Nov. 19, 2002

(54) METHOD AND APPARATUS FOR SEPARATING AND RECOVERING PERFLUORO COMPOUND

(75) Inventors: Fumio Kawasaki, Osaka (JP); Rosuke Matsubayashi, Osaka (JP)

(73) Assignee: Daido Air Products Electronics, Inc., Sakai (JP)

(*) Notice: Subject to any disclaimer, the term of this patent is extended or adjusted under 35 U.S.C. 154(b) by 0 days.

(21) Appl. No.: 09/926,044

(22) PCT Filed: Dec. 18, 2000

(86) PCT No.: PCT/JP00/08949
§ 371 (c)(1),
(2), (4) Date: Dec. 26, 2001

(87) PCT Pub. No.: WO01/45826
PCT Pub. Date: Jun. 28, 2001

(51) Int. Cl.⁷ .............................................. B01D 53/22
(52) U.S. Cl. ........................ 95/22; 95/23; 95/45; 95/47; 96/4; 96/9
(58) Field of Search ................ 95/19, 22, 23, 95/45, 47–56; 96/4, 9

(56) References Cited

U.S. PATENT DOCUMENTS

| | | | |
|---|---|---|---|
| 3,930,814 A | * 1/1976 | Gessner | 95/19 |
| 4,806,132 A | * 2/1989 | Campbell | 95/23 X |
| 4,857,082 A | * 8/1989 | DiMartino, Sr. et al. | 55/16 |
| 4,906,256 A | 3/1990 | Baker et al. | 55/16 |
| 5,064,446 A | * 11/1991 | Kusuki et al. | 55/16 |
| 5,281,253 A | * 1/1994 | Thompson | 95/22 |
| 5,425,801 A | * 6/1995 | Prasad | 95/22 X |
| 5,507,855 A | * 4/1996 | Barry | 95/22 X |
| 5,730,779 A | * 3/1998 | Chernyakov et al. | 95/47 X |
| 5,785,741 A | 7/1998 | Li et al. | 96/4 |
| 5,814,127 A | * 9/1998 | Li | 95/47 |
| 5,843,208 A | * 12/1998 | Anumakonda et al. | 95/47 |
| 5,976,222 A | * 11/1999 | Yang et al. | 95/47 X |
| 6,128,919 A | * 10/2000 | Daus et al. | 96/9 X |
| 6,197,090 B1 | * 3/2001 | Yamashita et al. | 95/22 X |
| 6,290,750 B1 | * 9/2001 | Ollivier et al. | 95/19 |

FOREIGN PATENT DOCUMENTS

| | | |
|---|---|---|
| EP | 0839568 A1 | 5/1998 |
| JP | 2000-218126 | 8/2000 |

OTHER PUBLICATIONS

International Search Report dated Apr. 10, 2001.

* cited by examiner

Primary Examiner—Robert H. Spitzer
(74) Attorney, Agent, or Firm—Armstrong, Westerman & Hattori, LLP (57) ABSTRACT

A PFC separation recovery method to separate and recover PFC by raising the pressure of diluted mixed gas consisting of PFC gas and diluent gas, and subsequently contacting the gas with a membrane which permeates more diluent gas than PFC gas, and to separate it into a permeable gas flow rich in diluent gas and a non-permeable gas flow rich in PFC gas; and a PFC separation recovery system therefor. Moreover, the method repeatedly separates the non-permeable gas flow into another permeable gas flow and another non-permeable gas flow by contacting the gas flow with another membrane having the same functions as those of the membrane; subsequently detecting the pressure or flow rate of the other permeable gas flow; and controlling the flow rate of the other non-permeable gas flow so as to make the pressure or flow rate constant.

8 Claims, 8 Drawing Sheets

METHOD AND APPARATUS FOR SEPARATING AND RECOVERING PERFLUORO COMPOUND

TECHNICAL FIELD

The present invention relates to a perfluoro compound separation recovery method to separate and recover a perfluoro compound with a membrane from diluted mixed gas in which the perfluoro compound is diluted, and a perfluoro compound separation recovery system therefor.

BACKGROUND ART

Perfluoro compound (simply mentioned as "PFC" hereinafter) gas such as $CF_4$, $C_2F_6$, $C_3F_8$, $C_4F_8$, $C_4F_{10}$, $CHF_3$, $SF_6$ and $NF_3$ has been conventionally diluted with a large amount of $N_2$ gas or the like for use such as in etching, cleaning a chamber and the like in the manufacturing process of semiconductors. Also, in the field of electrical machines, $SF_6$ is similarly used as insulating gas.

However, exhaust gas (diluted mixed gas) contains unreacted (undecomposed) PFC gas after use, causing such environmental problems as ozone layer depletion when the gas is released into the atmosphere.

Figure 8:
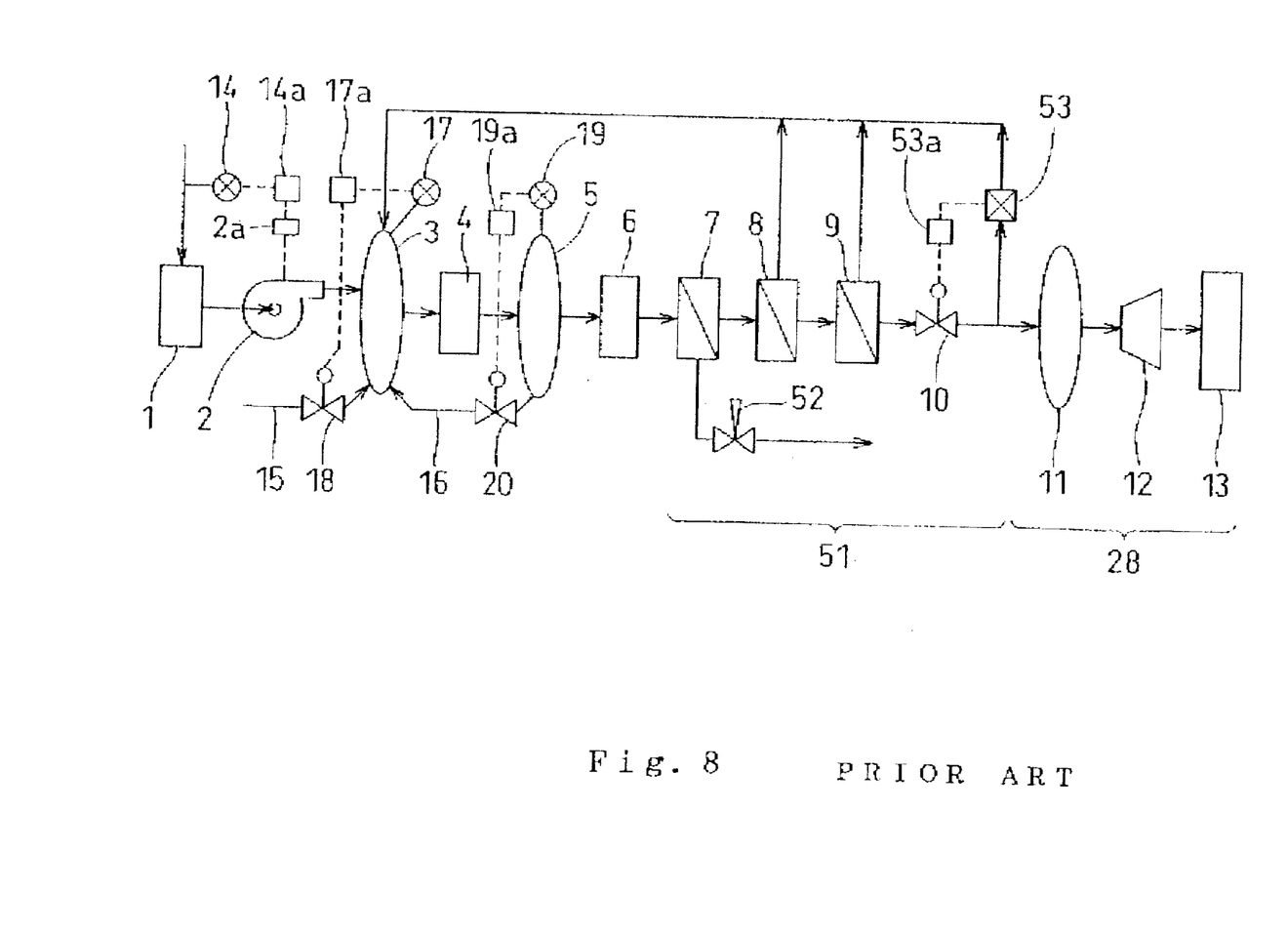
FIG. 8 is an explanatory diagram showing a conventional PFC separation recovery method and the PFC separation recovery system therefor.

Thus, PFC gas in exhaust gas has been conventionally recovered. A PFC separation recovery system shown in FIG. 8 is used to recover the gas. In the order of exhaust gas treatment, a pre-treatment unit 1, a blower 2, a first tank 3, a compressor 4, a second tank 5, a heat exchanger 6, a PFC separation unit 51 and a PFC recovery unit 28 are connected in series in the PFC separation recovery system.

More specifically, a first membrane 7, a second membrane 8 and a third membrane 9 ate arranged in series in the PFC separation unit 51. Each membrane 7, 8, 9 has a tendency to permeate more diluent gas such as N2 gas than PFC gas. The materials of each membrane 7, 8, 9 include polysulfone, polyetherimide, polypropylene, cellulose acetate, polymethylpentane, amorphous copolymer having 2,2-bistrifluoromethyl-4,5-difluoro-1,3-dioxysol as a radical, polyvinyltrimethylsilane, polyimide, polyamide, polyaramid or ethyl cellulose polymer, and the like. The materials mentioned above are formed in a hollow fiber, spiral, roll or flat sheet shape.

Moreover, spaces in the front and rear of each membrane 7, 8, 9 are a permeation side and a non-perineation side, respectively. The permeation side of the first membrane 7 is linked to the atmosphere through a needle valve 52, releasing permeated gas into the atmosphere. The non-permeation side of the first membrane 7 is connected to the second membrane 8. Also, the permeation side of the second membrane 8 is connected to return the gas to the first tank 3, and the non-permeation side of the second membrane 8 is connected to the third membrane 9. Furthermore, the permeation side of the third membrane 9 is connected to return the gas to the first tank 3, and the non-permeation side of the third membrane 9 is connected to the PFC recovery unit 28 through a first control valve 10.

Furthermore, a concentration analyzer 53 is provided to sample a portion of a third non-permeable gas flow between the first control valve 10 and the PFC recovery unit 28 so as to measure the concentration of PFC gas. A control unit 53a is also provided to control the opening of the first control valve 10 in response to the output of the concentration analyzer 53. In other words, when the concentration analyzer 53 takes in a portion of the third non-permeable gas flow and it is determined that the concentration of PFC gas is lower than a predetermined level, the control unit 53a reduces the opening of the first control valve 10, thus increasing a third permeable gas flow. Accordingly, diluent gas that was flowing to the non-permeation side flows to the permeation side, and recovery concentration (concentration of recovered PFC gas) improves. Thus, PFC gas of high concentration may be recovered by controlling the flow amount of the third non-permeable gas flow. The portion of the third non-permeable gas flow that was taken into the concentration analyzer 53 returns to the first tank 3 after the measurement of concentration.

A third tank 11, a booster pump 12 and a recovery container 13 are arranged in series in the PFC recovery unit 28.

The separation recovery of PFC gas is carried out as follows by the PFC separation recovery system. In other words, exhaust gas is first passed through the pre-treatment unit 1, removing an acid-based portion, a particle portion and the like which provide negative effects on the compressor 4 and each membrane 7, 8, 9, with a wet or dry scrubber, a filter and the like. Subsequently, the treated gas flow is stored in the first tank 3 by the blower 2. Then, the compressor 4 raises the pressure of a gas flow from the first tank 3 to store it in the second tank 5. The heat exchanger 6 raises the temperature of exhaust gas stored in the second tank 5. Then, the gas contacts the first membrane 7, thus separating the gas into a first permeable gas flow rich in diluent gas and a first non-permeable gas flow rich in PFC gas. Additionally, the first permeable gas flow is released into the atmosphere by opening and closing the needle valve 52. At the same time, the first non-permeable gas flow contacts the second membrane 8, thereby further separating the gas into a second permeable gas flow rich in diluent gas and a second non-permeable gas flow rich in PFC gas. Then, the second permeable gas flow is returned to the first tank 3. At the same time, the second non-permeable gas flow contacts the third membrane 9, thus separating the gas into a third permeable gas flow having diluent gas at high concentration and a third non-permeable gas flow having PFC gas at high concentration. Then, the third permeable gas flow is returned to the first tank 3. At the same time, the third non-permeable gas flow is stored into the third tank 11 through the first control valve 10. Subsequently, a gas flow from the third tank 11 is stored in the recovery container 13 by a booster pump 12. PFC gas can be separated and recovered as noted above.

In the above-noted PFC separation recovery method, pressure (internal pressure) is controlled at a constant level at the upstream side of the blower 2 and the upstream side (first tank 3) and the downstream side (second tank 5) of the compressor 4 for its stable operation.

In other words, a first pressure sensor 14 is provided before a section where exhaust gas flows into the PFC separation recovery system (the upstream side of the pre-treatment unit 1) in order to indicate the pressure of exhaust gas. Also, an inverter 2a is provided to the blower 2 to control its operation. At the same time, the inverter 2a is provided with a control unit 14a to send signals to itself in response to the output of the first pressure sensor 14. The inverter 2a starts the blower 2 to provide the output of the first pressure sensor 14 at a predetermined fixed level. Pressure at the upstream side of the blower 2 is controlled at a constant level thereby. The first pressure sensor 14 indicates strength values for sucking exhaust gas. The flow of exhaust gas is made stable and smooth by controlling the values so as to be constant.

As described above, gas flows into the first tank 3 after the blower 2, the permeation side of the second membrane 8, the permeation side of the third Membrane 9 and the concentration analyzer 53, and then flows out to the compressor 4. Additionally, there provided are a first line 15 to take in outside air, and a second line 16 returning from the second tank 5. At the same time, a second pressure sensor 17 is provided to indicate the internal pressure of the first tank 3. Furthermore, a second control valve 18 is Provided at the first line 15, and a control unit 17a is provided to the second control valve 18 to control its opening in response to the output of the second pressure sensor 17. The second tank 5 is also provided with a third pressure sensor 19 to show its internal pressure. Furthermore, the second line 16 is provided with a third control valve 20, and a control unit 19a is provided to the third control valve 20 to control its opening in response to the output of the third pressure sensor 19. The internal pressure of the first tank 3 is controlled at a constant level by controlling the second control valve 18 of the first line 15. The internal pressure of the second tank 5 is controlled at a constant level by controlling the third control valve 20 of the second line 16. In other words, when the amount of gas flowing from the blower 2 into the first tank 3 decreases, the second control valve 18 is gradually opened to supplement a deficient amount of gas with outside air, thus controlling the internal pressure of the first tank 3 at a constant level. This control is achieved by controlling the internal pressure of the first tank 3 (set pressure of the second pressure sensor 17) at a negative level.

However, in the conventional art mentioned above, the expensive concentration analyzer 53 is necessary to control the first control valve 10. It is also necessary to perform fine concentration adjustment to raise recovery concentration to a limit so as to provide a recovery rate (a rate between the amount of recovered PFC gas and the amount of exhaust gas) at a predetermined level or higher. Thus, the concentration analyzer 53 of extremely high precision becomes necessary. Moreover, since the concentration analyzer 53 requires time for concentration detection, the output thereof becomes inevitably intermittent. It is also difficult to respond to periodic changes in the state of exhaust gas (exhaust timing of exhaust gas, flow amount of exhaust gas, concentration of PFC gas in exhaust gas, types of PFC gas in exhaust gas, and so forth). Therefore, even if controlled to reach predetermined recovery concentration, it is essentially impossible to stabilize recovery concentration. (See dotted line in FIG. 4.)

Also, the internal pressure of the first tank 3 is controlled at a constant level by taking in outside air in the conventional art mentioned above, so that the following problems (1) to (4) exist. (1) Exhaust gas is diluted as outside air is taken in, so that the recovery efficiency of PFC declines. (2) When the level of negative pressure of the first tank 3 becomes small (close to the atmospheric pressure) by taking in outside air, the control range of the internal pressure of the first tank 3 becomes small and it becomes difficult to respond to the flow rate fluctuations or the like of exhaust gas. As a result, it becomes difficult to control the internal pressure of the first tank 3 at a constant level. (3) Only when the internal pressure of the first tank 3 (output of the second pressure sensor 17) is constant, can pressure at the upstream side of the blower 2 (output of the first pressure sensor 14) be controlled at an accurate target level by controlling the blower 2 which uses the inverter 2a. However, as described above, it is difficult to set the internal pressure of the first tank 3 at a constant level due to a change in the state of exhaust gas. Thus, it becomes difficult to control the pressure on the upstream side of the blower 2 (output of the first pressure sensor 14) at an accurate target level. (4) In order to enlarge a control range of the internal pressure of the first tank 3, the level of negative pressure has to be large in advance so as not to reduce the level of negative pressure of the first tank 3 even when outside air is taken in. when the level of the negative pressure of the first tank 3 is large, the load of the compressor 4 that raises the pressure of a gas flow from the first tank 3 becomes high, Accordingly, the running cost of the compressor 4 increases.

The present invention was made considering these circumstances. Its object is to provide a perfluoro compound separation recovery method which can stabilize recovery concentration while sensitively responding to a change in the state of exhaust gas, and which can lower the costs of a separation recovery system, and a perfluoro compound separation recovery system therefor.

DISCLOSURE OF INVENTION

In order to achieve the object above, a first aspect of the present invention is a perfluoro compound separation recovery method which separates and recovers perfluoro compound gas by contact with a membrane which permeates more diluent gas than perfluoro compound gas, after the pressure of diluted mixed gas consisting of perfluoro compound gas and diluent gas is raised high. The method includes the steps of separating high-pressurized diluted mixed gas into a permeable gas flow rich in diluent gas and a non-permeable gas flow rich in perfluoro compound,gas by contact with the above-mentioned membrane; repeatedly separating the non-permeable gas flow into another permeable gas flow and another non-permeable gas flow by contact with another membrane having the same functions as those of the membrane mentioned above; detecting the pressure or flow rate of the other permeable gas flow; controlling the flow rate the other non-permeable gas flow so as to set the pressure or flow rate constant; and recovering the other non-permeable gas flow. A second aspect of the present invention is a perfluoro compound separation recovery system having a means to raise the pressure of diluted mixed gas consisting of perfluoro compound gas and diluent gas; and a membrane to separate high-pressurized diluted mixed gas into a permeable gas flow rich in diluent gas and a non-permeable gas flow rich in perfluoro compound gas. The system includes another membrane to separate the above-noted non-permeable gas flow into another permeable gas flow and another non-permeable gas flow; a means to detect the pressure or flow rate of the other permeable gas flow; a means to control the flow rate of the other non-permeable gas flow; and a means to recover the other non-permeable gasflow.

The present inventors repeated thorough studies on the perfluoro compound separation recovery method and the perfluoro compound separation recovery system therefor. As a result, by providing constant pressure or flow rate of the other permeable gas mentioned above (gas rich in diluent gas which is provided by repeatedly separating the non-permeable flow that was separated with an initial membrane and is rich in PFC gas, with another membrane), nearly no fluctuations were found in the concentration of PFC gas after treatment, even if the concentration of PFC gas was uneven in diluted mixed gas to be treated, thereby achieving the present invention.

In other words, the perfluoro compound separation recovery method of the present invention includes the steps of detecting the pressure or flow rate of the other permeable gas flow; and controlling the flow rate of the other non-permeable gas flow so as to make the pressure or flow rate constant. Thus, even if there are fluctuations in the concentration of PFC gas in diluted mixed gas, the concentration of PFC gas after treatment can be kept roughly constant.

When the perfluoro compound separation recovery method of the present invention includes the step of controlling the pressure of diluted mixed gas at a predetermined fixed level before increasing the pressure of diluted mixed gas by returning an appropriate amount of the permeable gas flow to diluted mixed gas, and when the control is carried out without taking in outside air in the step, diluted mixed gas is not diluted with outside air. Thus, the recovery efficiency of PFC improves. Since outside air is not taken in when the pressure of diluted mixed gas before the pressure increase is controlled constant as mentioned above, the control range of the pressure of diluted mixed gas before the pressure increase is not reduced, Therefore, even if the states of the diluted mixed gas change, the method can easily respond to the change. Moreover, as outside air is not taken in as mentioned above, the load can be reduced when the pressure of diluted mixed gas is increased.

Since the perfluoro compound separation recovery system of the present invention has a means to detect the pressure or flow rate of the other permeable gas flow, an expensive concentration analyzer is unnecessary and costs can be reduced. Furthermore, since pressure or flow rate can be continuously detected, the system can respond to the periodic changes of the state of exhaust gas, and the concentration of PFC gas after treatment can be kept roughly constant.

BEST MODE FOR CARRYING OUT THE INVENTION

An embodiment of the present invention will be explained in detail based on drawings.

Figure 1:
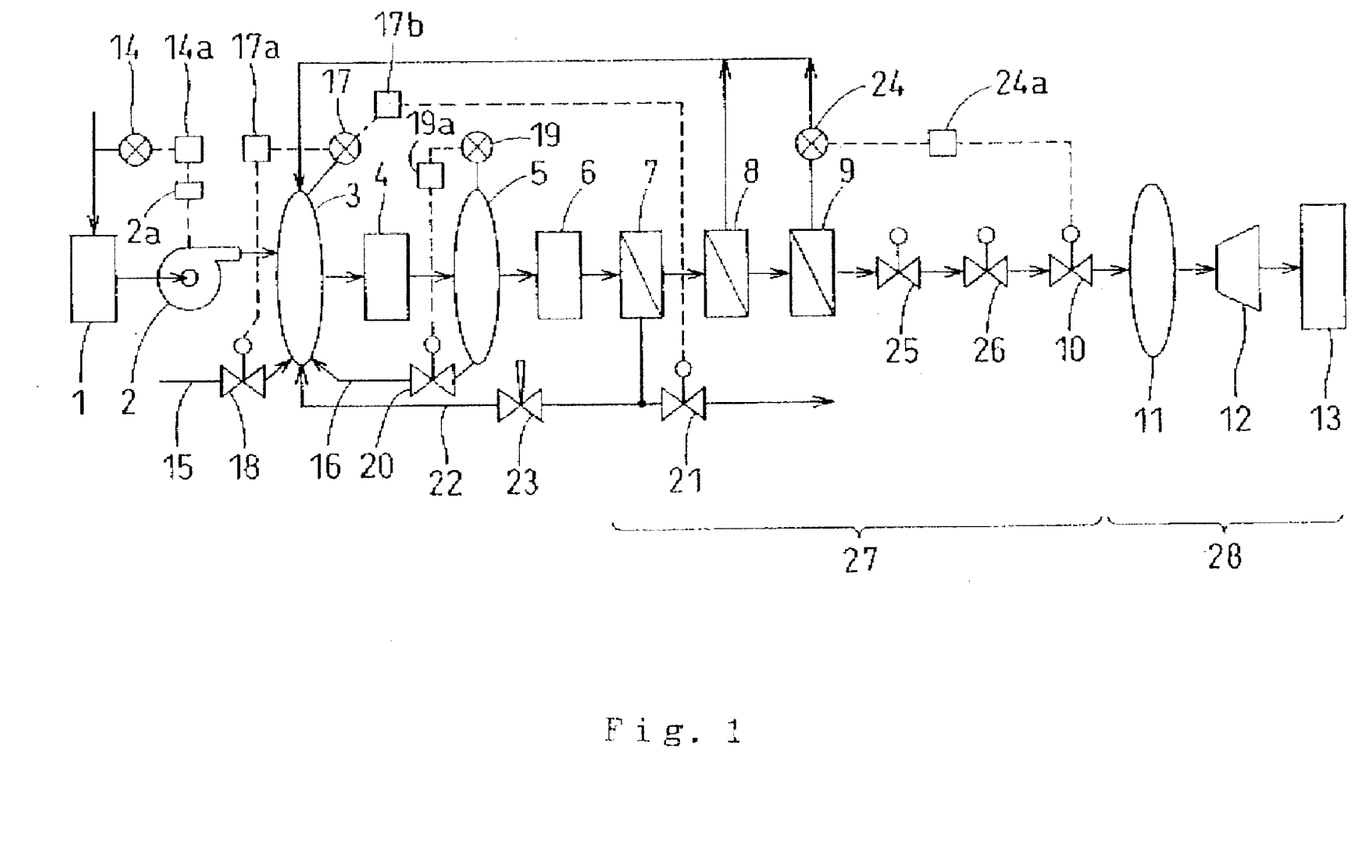
FIG. 1 is an explanatory diagram showing an embodiment of the PFC separation recovery method and the PFC separation recovery system therefor of the present invention.

FIG. 1 shows an embodiment of the perfluoro compound separation recovery method and the perfluoro compound separation recovery system therefor of the present invention. Parts that are different from those of the conventional art shown in FIG. 8 are mainly explained herein, and the same reference numerals are used for the identical parts and the specific description thereof is omitted.

Figure 2:
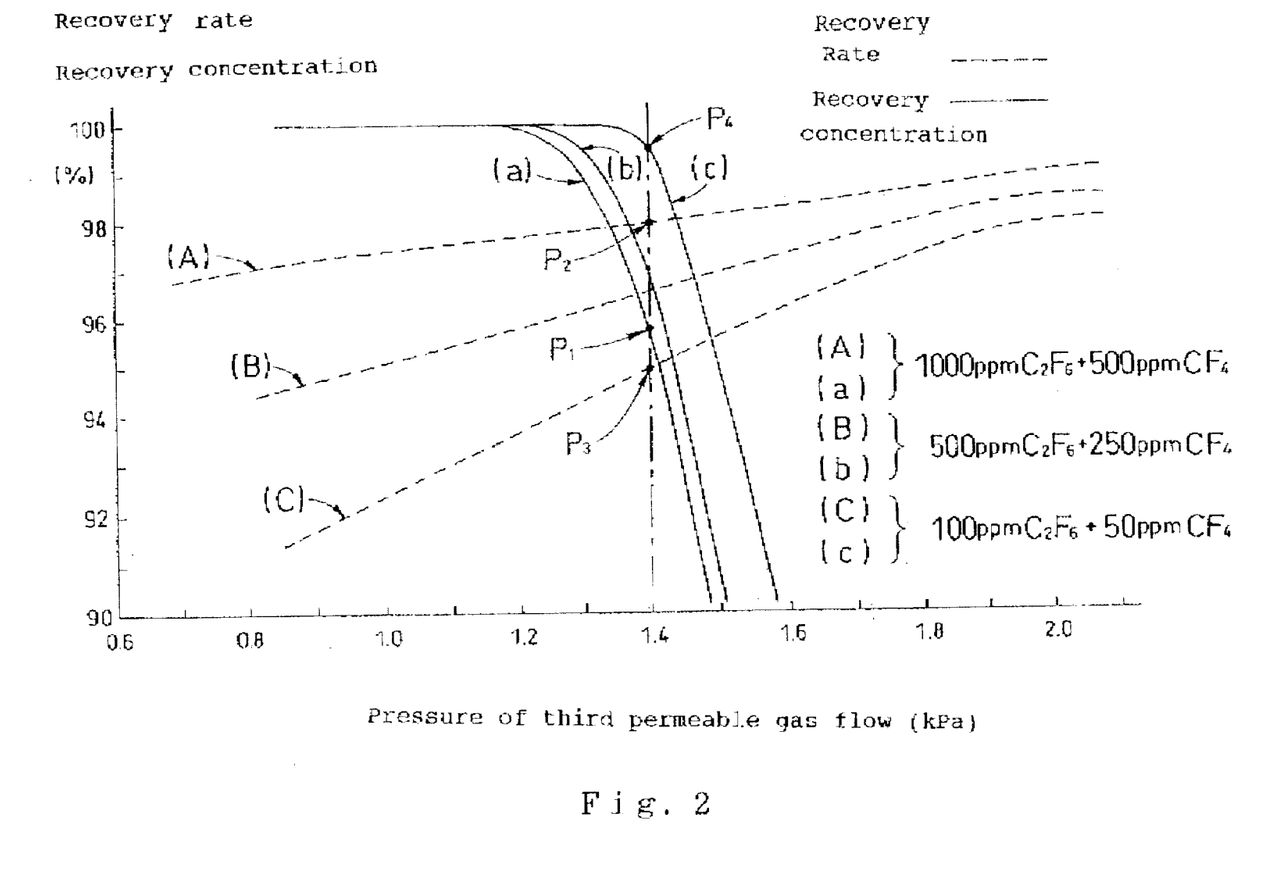
FIG. 2 is a graph showing relations between the pressure of a third permeable gas flow and recovery rate, and recovery concentration in the above-noted PFC separation recovery method and the PFC separation recovery system therefor.

In other words, this perfluoro compound (PFC) separation recovery system has a fourth control valve 21, instead of a needle valve 52 on the permeation side of the first membrane 7 in the conventional art shown in FIG. 8, and has a third line 22 which branches out from the upstream side of the fourth control valve 21 and which returns to the first tank 3. The third line 22 has a needle valve 23, and a fourth control valve 21 has a control unit 17b which can control its opening in response to the output of the second pressure sensor 17. Furthermore, the perfluoro compound (PFC) separation recovery system of this embodiment has a fourth pressure sensor 24 on the permeation side of the third membrane 9, instead of the concentration analyzer 53 in the conventional art shown in FIG. 8. A control unit 24a is also provided to feedback-control the opening of the first control valve 10 so as to constantly stabilize the output of the fourth pressure sensor 24 and show a predetermined fixed pressure. Moreover, a first regulator 25 and a second automatic pressure regulator 26 are sequentially arranged in series between the non-permeation side of the third membrane 9 and the first control valve 10. Other parts are the same as those in the conventional PFC separation recovery system shown in FIG. 8, In the PFC separation recovery system shown in FIG. 1, the relationships between the pressure of a third permeable gas flow (output of the fourth pressure sensor 24) and recovery rate, and recovery concentration are as shown in FIG. 2. Exhaust gases containing $C_2F_6$ and $CF_4$ as PFC gas at different concentrations are used in FIG. 2. An example of targeting both recovery rate and recovery concentration at 95% or higher in FIG. 2 will be explained.

When the concentration of PFC gas in the exhaust gas is high, the recovery rate (curve A) is 95% or higher at any pressure of the third permeable gas flow. The recovery concentration (curve a) is 95% or higher when the pressure of the third permeable gas flow is not more than 1.41 kPa. When the concentration of PFC gas in the exhaust gas is intermediate, the recovery rate (curve B) is 95% or higher when the pressure of the third permeable gas flow is 0.95 kPa or higher. The recovery concentration (curve b) is 95% or higher when the pressure of the third permeable gas flow is not more than 1.43 kPa.

When the concentration of PFC gas in the exhaust gas is low, the recovery rate (curve C) is 95% or higher when the pressure of the third permeable gas flow is 1.39 kPa or higher. The recovery concentration (curve c) is 95% or higher when the pressure of the third permeable gas flow is not more than 1.49 kPa.

Accordingly, both recovery rate and recovery concentration become 95% or higher when the pressure of the third permeable gas flow is in the range of 1.39 to 1.41 kPa. Therefore, when the control valve is controlled to constantly keep the pressure of the third permeable gas flow at about 1.40 kPa, both recovery rate and recovery concentration can be 95% or higher.

Either recovery rate or recovery concentration can be prioritized for control in the above-noted embodiment. In other words, the pressure of the third permeable gas flow is in the range of 0.95 to 1.49 kPa in order to set both recovery rate and recovery concentration at 95% or higher at each curve of A, a, B, b, C and c curves. By controlling the control valve to constantly maintain 1.40 kPa in this range (see a chain line in the figure), the recovery concentration is low (point $P_1$) but the recovery rate is high (point $P_2$) when the concentration of PFC gas in the exhaust gas is high (curves A, a). When the concentration of PFC gas in exhaust gas is low (curves C, c), the recovery rate is low (point $P_3$) but the recovery concentration is high (point $P_4$).

Figure 3:
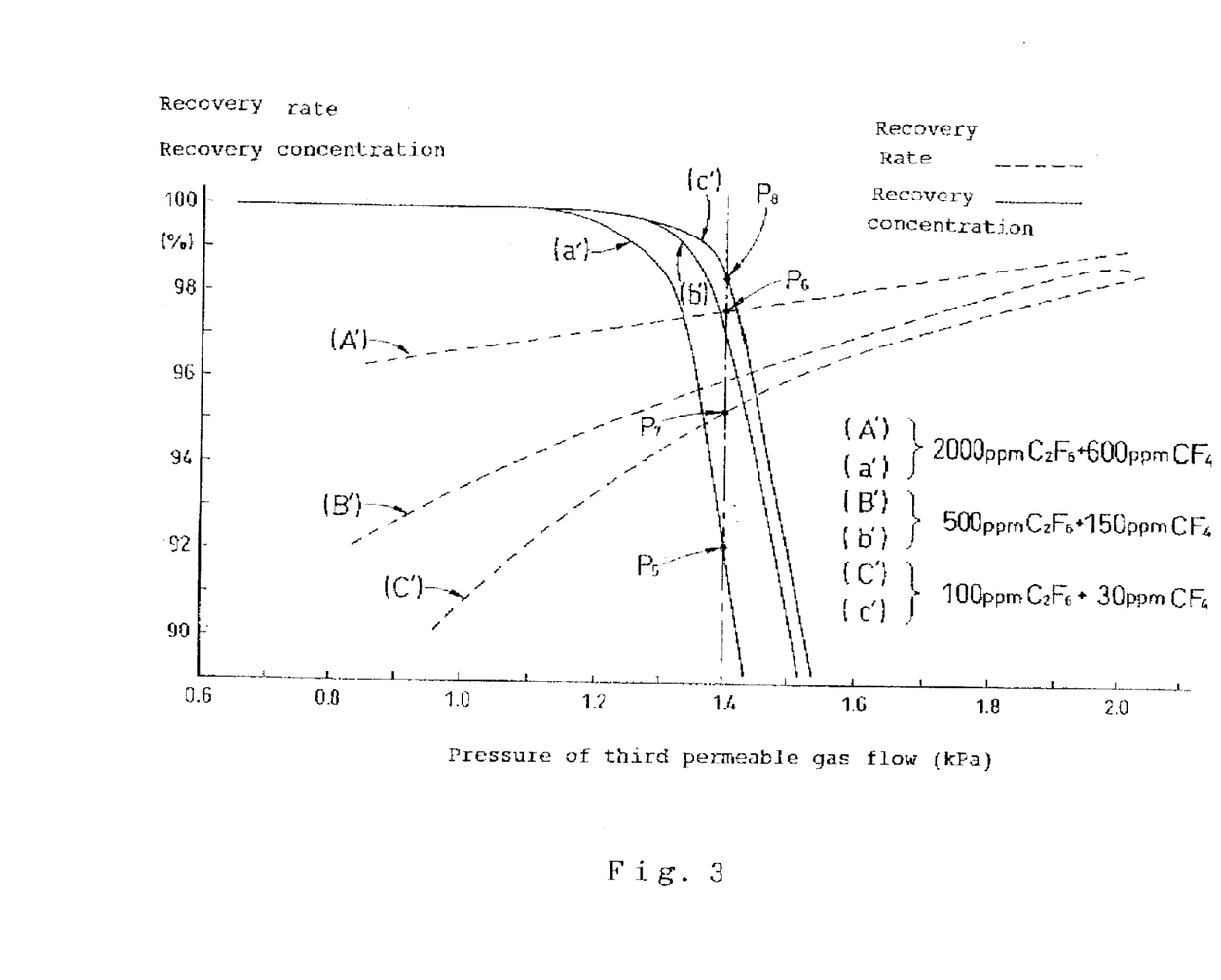
FIG. 3 is a graph showing the above-noted relations when the composition of PFC gas in exhaust gas changes in the above relations between the pressure of a third permeable gas flow and recovery rate and recovery concentration.

Furthermore, even when the composition of PFC gas in the exhaust gas changes (see FIG. 3), the same relationships as those shown in FIG. 2 are seen. By controlling the control valve to constantly maintain the pressure of the third permeable gas flow at 1.40 kPa as mentioned above (see a chain line in the figure), the recovery concentration is low (point $P_5$) but the recovery rate is high (point $P_6$) when the concentration of PFC gas in the exhaust gas is high (curves A', a'). when the concentration of PFC gas in the exhaust gas is low (curves C', c'), the recovery rate is low (point $P_7$) but the recovery concentration is high (point $P_8$). The composition shows a distinctive range (recovery rate of 95.3 to 97.8%; recovery concentration of 91.3 to 97.8%).

In general, recovery concentration decreases when recovery rate is controlled to be higher in a PFC separation recovery method using membranes. To the contrary, when recovery concentration is controlled to be higher, recovery rate declines. In the conventional art mentioned above, the recovery concentration of PFC gas is controlled, but recovery rate is not controlled. The conventional art cannot specifically determine the state of the exhaust gas flowing into a PFC separation recovery system. Thus, when only a control to raise recovery concentration is performed, there has been a problem in that even a change in the state of the exhaust gas to lower recovery rate cannot be determined and the control is continued. Also, there are PFC gases from which high recovery rate and recovery concentration can be expected, and those from which generally low recovery rate and recovery concentration are expected. Thus, even if the control is performed to obtain predetermined recovery concentration as in the conventional art, recovery rate cannot become satisfactory when the composition changes at one point from one gas from which high recovery rate is obtained, to another gas from which only low recovery rate can be obtained.

However, when the pressure of the third permeable gas flow (output of the fourth pressure sensor 24) is made constant as in the embodiment mentioned above, either high recovery rate or high recovery concentration is prioritized even when the state of the exhaust gas varies. The non-prioritized one can also be set above the minimum level.

Pressures at the upstream side of the blower 2 and at the upstream side (first tank 3) and the downstream side (second tank 5) of the compressor 4 are also controlled to be constant in the above-noted embodiment. However, the control of pressure (internal pressure) on the upstream side (first tank 3) of the compressor 4 is different from that in the conventional art shown in FIG. 8. In other words, as described above, gas flows into the first tank 3 from the blower 2, the first line 15 (outside air), the second line 16 (second tank 5), the third line 22 (line branched from the permeation side of the first membrane 7), the permeation side of the second membrane 8 and the permeation side of the third membrane 9 (fourth pressure sensor 24), and flows out to the compressor 4. The internal pressure of the first tank 3 is controlled to be constant by controlling the fourth control valve 21 on the permeation side of the first membrane 7 and adjusting the opening of the needle valve 23 of the third line 22. In other words, when the amount of gas flowing from the blower 2 to the first tank 3 decreases, the opening of the fourth control valve 21 is controlled without taking in outside air from the first line 15. At the same time, a portion of a first permeable gas flow is taken in from the third line 22 by adjusting the opening of the needle valve 23 of the third line 22. Thus, deficient gas is supplemented, and the pressure of the first tank 3 is controlled to be constant, However, when deficient gas is not supplemented even by the process mentioned above, the second control valve 18 of the first line 15 is used to take in outside air. In other words, the purpose of the second control valve 18 is different from that of the conventional art shown in FIG. 8, and the valve is used not for normal operations but only for an emergency.

The function of the needle valve 23 of the third line 22 is explained herein. The needle valve 23 has a function to generate a resistance to the gas flow of the third line 22 and adjust a flow rate which can be controlled by the fourth control valve 21. In other words, for instance, the internal pressure of the first tank 3 is controlled at atmospheric pressure, and the opening of the needle valve 23 is set at 100%. In this case, roughly the entire first permeable gas flow can be released when the downstream side (discharge destination) of the fourth control valve 21 is at negative pressure and the opening of the fourth control valve 21 is 100%. However, when the downstream side (discharge destination) of the fourth control valve 21 is at positive pressure or atmospheric pressure, the entire first permeable gas flow cannot be discharged even by opening the fourth control valve 21 at 100%. The gas naturally flows into the first tank 3 (third line 22). Then, when the opening of the needle valve 23 is 0% in the state (in which the downstream side of the fourth control valve 21 is at positive pressure or atmospheric pressure, and the opening of the fourth control valve 21 is 100%), the needle valve 23 operates to discharge roughly the entire first permeable gas flow without depending on the internal pressure of the first tank 3. In other words, as a resistance to the gas flow of the third line 22 is increased by reducing the opening of the needle valve 23, the fourth control valve 21 can control a wider range of flow rates. Thus, the flow rate control range of the fourth control valve 21 is changed by adjusting the opening of the needle valve 23 on the basis of pressure at the downstream side of the fourth control valve 21. The flow rate of the first permeable gas flow, which is discharged and returned to the first tank 3, is controlled within the flow rate control range by controlling the opening of the fourth control valve 21.

Moreover, the PFC separation unit 27 returns the third permeable gas flow, which was separated at the third membrane 9, to the first tank 3 through the fourth pressure sensor 24. At the same time, the third non-permeable gas flow is stored in the third tank 11 sequentially throughout the first regulator 25, the second automatic pressure regulator 26 and the first control valve 10.

The functions of the first regulator 25, the second automatic pressure regulator 26, the first control valve 10, and the third tank 11 are explained hereinafter.

The first regulator 25 improves the flow rate control of the first control valve 10, so that its purpose is to set the pressure at the first control valve 10 low.

The second automatic pressure regulator 26 has the purpose of constantly controlling the inlet pressure of the first control valve 10 at a fixed level at any opening state of the first control valve 10 connected at the downstream thereof, and to instantly achieve the maximum flow rate control of the first control valve 10. The second automatic pressure regulator 26 has a function to constantly monitor pressure on the downstream side, to recognize a difference between set pressure and current pressure and to keep a constant set pressure by adjusting the pressing level of its spring so as to restore to the set pressure. The purpose of connecting it in series along with the first regulator 25 is to reduce a pressure difference between its upstream side and downstream side so as to maximize the pressure governing function of the second automatic pressure regulator 26 itself.

The first control valve 10 has a function to adjust the ratio between the amount of the third permeable gas flow and the amount of the third non-permeable gas flow, and this adjustment determines recovery rate and recovery concentration. In other words, when the first control valve 10 operates in a closing direction, resistance to the non-permeation side increases and recovering PFC gas flows to the permeation side. Accordingly, recovery rate decreases. However, as diluent gas which was flowing to the non-permeation side, also flows towards the permeation side, recovery concentration improves. To the contrary, when the first control valve 10 operates in an opening direction, resistance to the non-permeation side decreases and PFC gas, which was flowing to the permeation side, flows towards the non-permeation side. Accordingly, recovery rate improves. However, as diluent gas which was flowing to the permeation side, also flows to the non-permeation side, recovery concentration decreases.

The third tank 11 has a purpose to fully achieve the flow rate control function of the first control valve 10. In other words, if the third non-permeable gas flow which passed through the first control valve 10, is directly connected to the booster pump 12 without the third tank 11, the booster pump 12 treats an amount (an amount that the booster pump 12 can treat) that is different from the amount of the third non-permeable gas flow adjusted at the first control valve 10. Thus, the pressure at the downstream side of the first control valve 10 changes. However, the flow rate control function of the first control valve 10 is influenced by a pressure difference between its upstream side and downstream side. Therefore, the pressure at the downstream side of the first control valve 10 is kept constant by providing the third tank 11.

Subsequently, a manner to confirm the concentration of PFC gas in the exhaust gas flowing into a PFC separation A recovery system (degree of non-permeability) will be explained.

The absolute amount of a permeable gas flow that can permeate through the first membrane 7, the second membrane 8, and the third membrane 9, affects the temperature and the pressure thereof, and the concentration of non-permeable gas in the inflow gas (in this case, concentration and compositions of several types of PFC gas in the entire exhaust gas).

When the opening of the first control valve 10 is kept constant (a gas flow is kept constant at the first control valve 10) and PFC gas to be separated flows into a PFC separation recovery system at a high concentration relative to diluent gas, the absolute amount of PFC gas in each membrane 7, 8, 9 is large (in comparison with the case when the PFC gas flows in at a low concentration). Therefore, when an exhaust gas of high PFC gas concentration is flowing into a PFC separation recovery system, the flow rate of the first to third permeable gas flows decreases naturally. Additionally, each flow rate of the first to the third permeable gas flows decreases further, sequentially, from the first membrane 7 to the third membrane 9 (even when the concentration of PFC gas in the inflow exhaust gas is constant). This phenomenon is clearly found in the third permeable gas flow. In other words, the pressure of the third permeable gas flow declines. To the contrary, when an exhaust gas of low PFC gas concentration is flowing into a PFC separation recovery system, something reverse to the above is seen, and the pressure of the third permeable gas flow rises.

Thus, the pressure of the third permeable gas flow (output of the fourth pressure sensor 24) can be used as a parameter to determine the concentration of PFC gas (degree of non-permeability) in the exhaust gas flowing into a PFC separation recovery system. Accordingly, if the relationships between the pressure of the third permeable gas flow and the concentration of PC gas in the exhaust gas (degree of non-permeability) are determined in advance, each correlation can be understood.

Subsequently, when not only can the concentration of PFC gas (degree of non-permeability) in the exhaust gas be determined, but also the pressure of the third permeable gas flow is forcibly controlled to be constant (in other words, in the case that the pressure is adjusted to be the same as the pressure when the concentration is high even when the concentration of PFC gas (degree of non-permeability) in the exhaust gas is low), it can be said that the presence rate of PFC gas which stays in the third membrane 9 is controlled to be constant.

Therefore, this indicates that the pressure of the third permeable gas flow shows the presence rate of PFC gas which stays in the third membrane 9, and that controlling the pressure of the third permeable gas flow constant determines the PFC gas recovery function of the third membrane 9.

Whether or not PFC gas in an exhaust gas is a material from which high recovery rate and high recovery concentration can be expected, is important in the step of concentrating PFC gas in the exhaust gas for recovery. A specific material name and concentration and mixing ratios indicates apparent permeation difficulty of one kind of PFC gas through the third membrane 9 is determined, whether or not PFC gas can be efficiently recovered (with high recovery rate and high recovery concentration) is satisfied.

Examples will be explained along with a conventional example and comparative examples.

EXAMPLE 1

Figure 4:
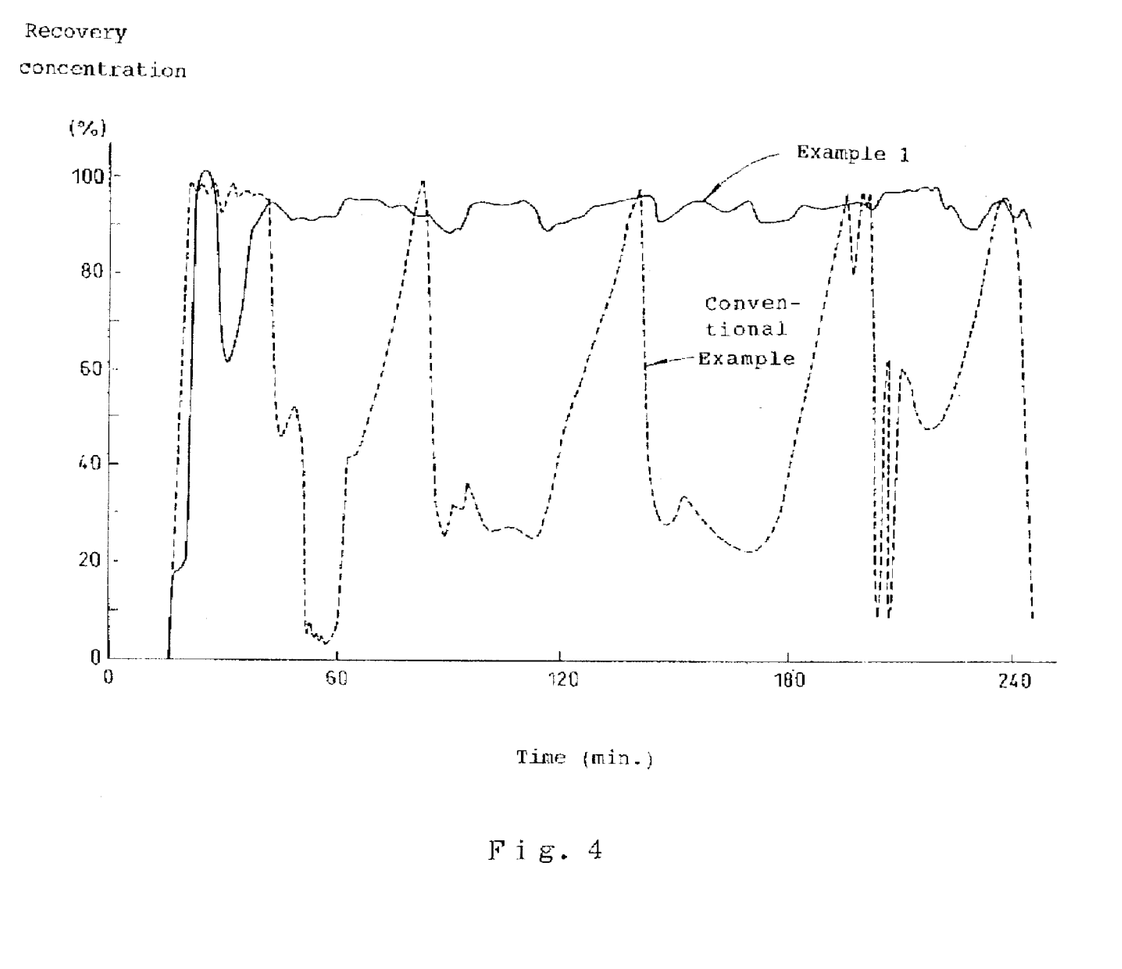
FIG. 4 is a graph showing recovery concentration when PFC gas is recovered by the above-noted PFC separation recovery method and the PFC separation recovery system therefor, and recovery concentration when PFC gas is recovered by a conventional art.

FIG. 4 shows, in a solid line, the recovery concentration when PFC gas was recovered in the above-noted embodiment. According to the results, the recovery concentration was stable and high.

CONVENTIONAL EXAMPLE

FIG. 4 shows, in a dotted line, the recovery concentration when PFC gas was recovered in the above-noted conventional embodiment. According to the result, the recovery concentration was unstable and was often extremely low.

It can be understood from FIG. 4 that Example 1 can easily respond to a change in the state of the exhaust gas, but such a response is difficult in the conventional example.

EXAMPLE 2

Figure 5:
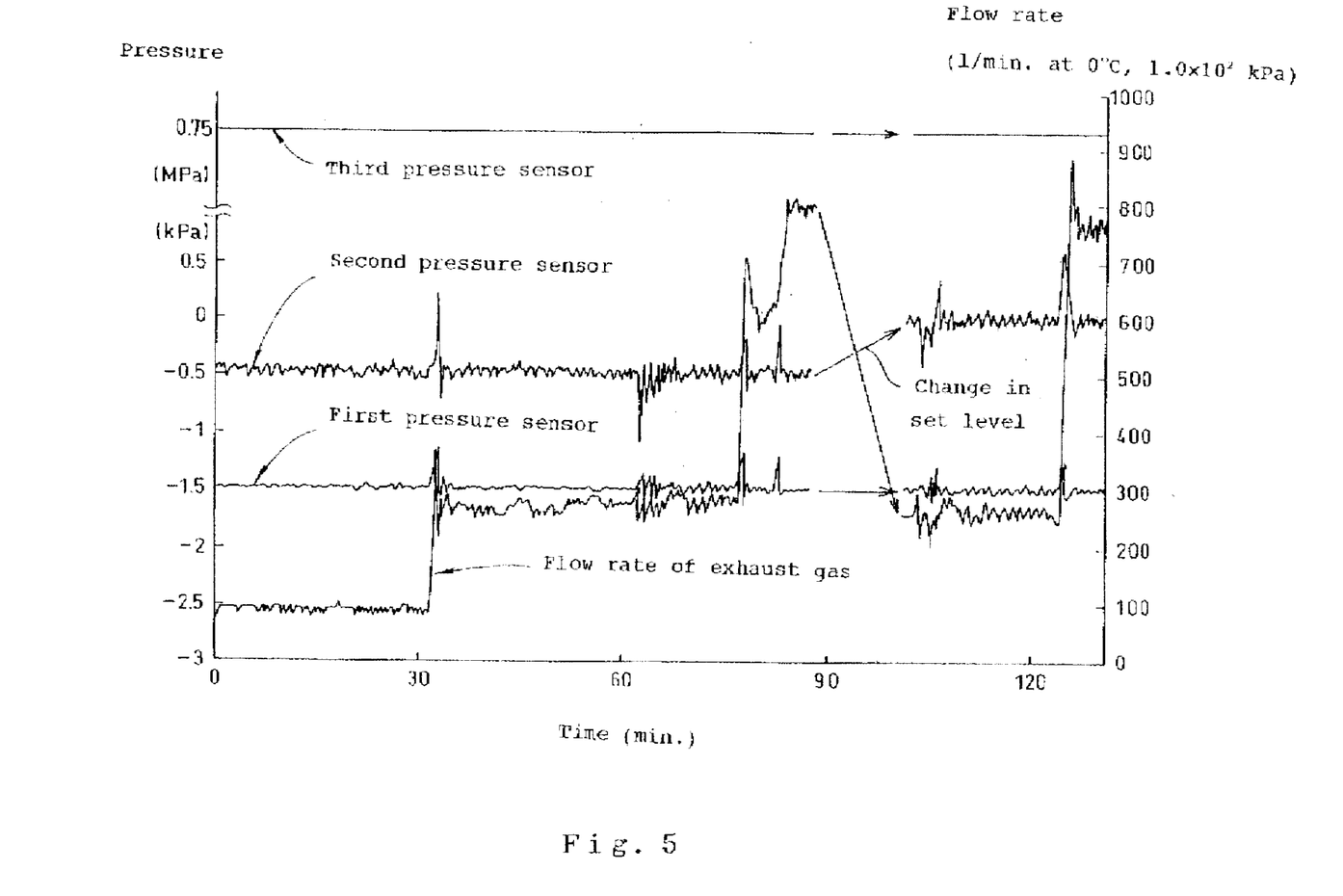
FIG. 5 is a graph showing the output of a first to third pressure sensor when the flow rate of exhaust gas fluctuates in the above-noted PFC separation recovery method and the PFC separation recovery system therefor.

FIG. 5 shows pressure on the upstream side of the blower 2 (output of the first pressure sensor 14) and internal pressure on the upstream side (first tank 3) of the compressor 4 (output of the second pressure sensor 17) and internal pressure on the downstream side (second tank 5) of the compressor 4 (output of the third pressure sensor 19) when the flow rate of the exhaust gas flowing into a PFC separation recovery system was changed in the embodiment. FIG. 5 shows the output of the first to third pressure sensors 14, 17 and 19 when the set level of the second pressure sensor 17 was changed from −0.50 kPa to near atmospheric pressure.

It can be observed from FIG. 5 that the internal pressure of the first tank 3 (output of the second pressure sensor 17) is always roughly constant at a set level even when the flow rate of the exhaust gas changes. It also can be observed that a reset level is kept constant even after the set level of the second pressure sensor 17 is reset. Thus, since the internal pressure of the first tank 3 is kept constant, pressure on the upstream side of the blower 2 as well as pressure on the downstream side of the compressor 4 can be kept constant.

EXAMPLE 3

Figure 6:
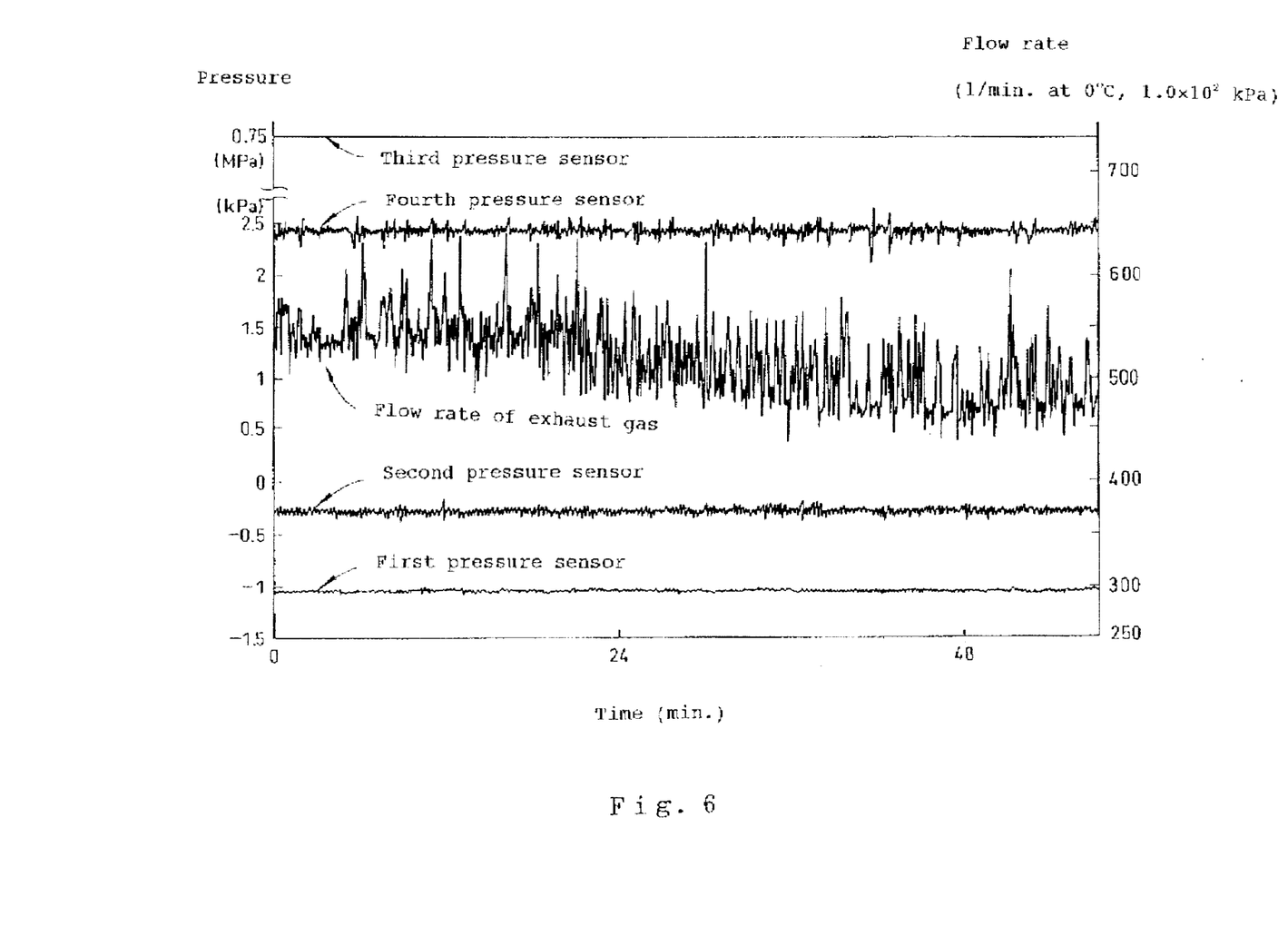
FIG. 6 is a graph showing the output of a first to fourth pressure sensor when the flow rate of exhaust gas fluctuates and is examined over a long period in the above-noted PFC separation recovery method and the PFC separation recovery system therefor.

The flow rate of the exhaust gas flowing into a PFC separation recovery system was changed in this embodiment, and FIG. 6 shows the output of the first to fourth pressure sensors 14, 17, 19 and 24 when the experiment was performed over a long period.

It can be observed from FIG. 6 that the output of the fourth pressure sensor 24 (pressure of the third permeable gas flow) can also be kept constant. Thus, it becomes possible to perform the PFC separation recovery method of the embodiment in which the fourth pressure sensor 24 is provided to the third permeable gas flow and the downstream thereof is connected to the first tank 3.

COMPARATIVE EXAMPLE

Figure 7:
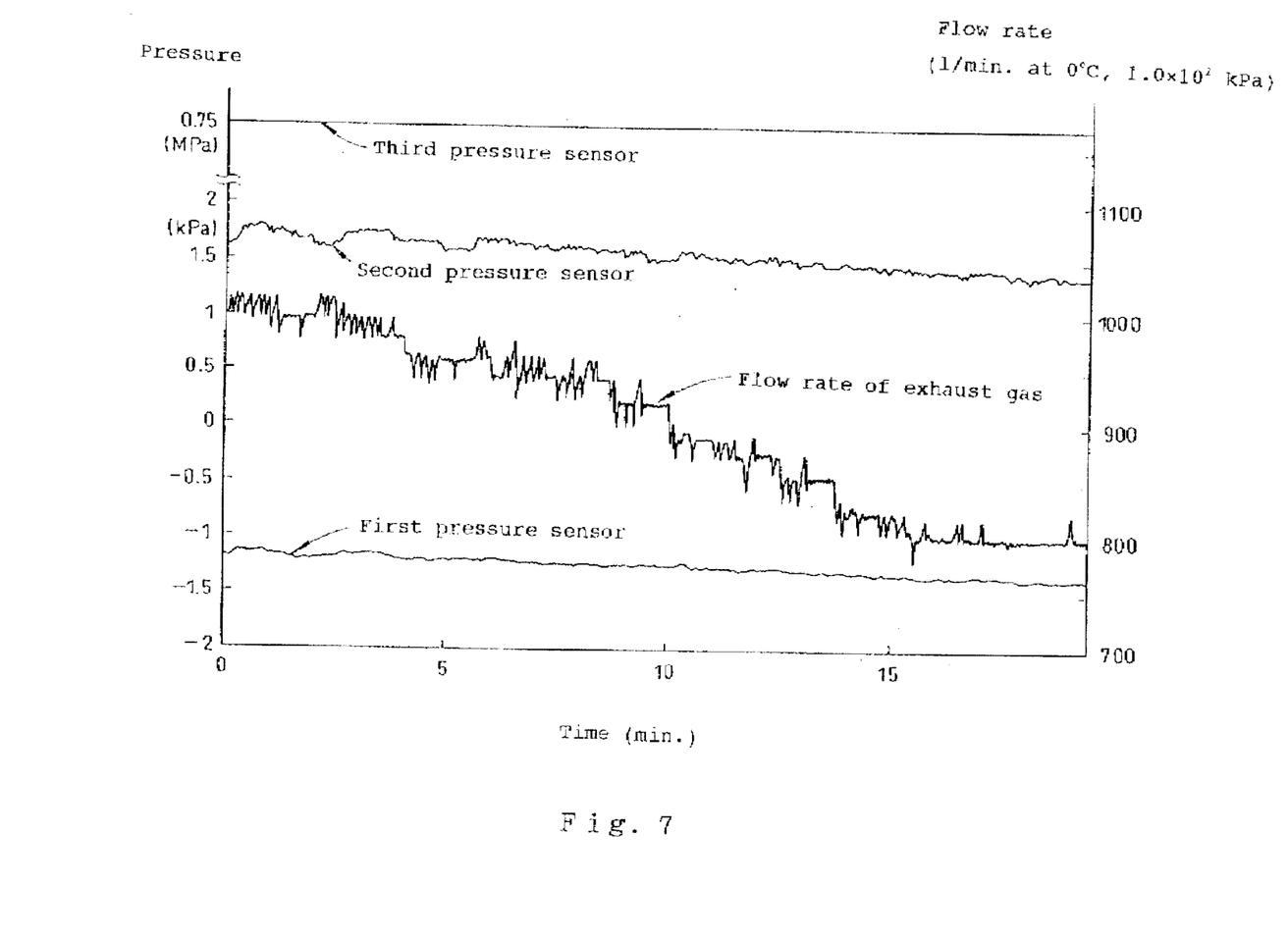
FIG. 7 is a graph showing the output of a first to third pressure sensor when the flow rate of exhaust gas fluctuates without constant pressure control by a second pressure sensor in the above-noted PFC separation recovery method and the PFC separation recovery system therefor.

FIG. 7 shows the output of the first to third pressure sensors 14, 17 and 19 when the flow rate of an exhaust gas flowing into a PFC separation recovery system is changed without controlling pressure at constant pressure by the second pressure sensor 17.

It can be observed from FIG. 7 that the output of the first pressure sensor 14 (pressure on the upstream side of the blower 2) has the same waveform due to the effect of the output of the second pressure sensor 17 (internal pressure of the first tank 3). Thus, it is found that pressure on the upstream side of the blower 2 is likely to be affected as fine pressure control. Also, the control pressure of the third pressure sensor 19 is different from the control pressure of the second pressure sensor 17 by three digits, so that it does not seem to be much affected.

Thus, according to the above-noted embodiment, the fourth pressure sensor 24 is provided on the permeation side of the third membrane 9; the first control valve 10 is provided on the non-permeation side of the third membrane 9; and the opening of the first control valve 10 is feedback-controlled by the control unit 24a so as to constantly stabilize the output of the fourth pressure sensor 24 and show a predetermined constant pressure. Thus, either high recovery rate or high recovery concentration can be prioritized for control. Moreover, the one that was not prioritized can be controlled at the minimum level or higher. Therefore, diluent gas, contained in recovering third non-permeable gas flow, decreases. Accordingly, the booster pump 12 for use in recovery can be made energy efficient during operation, and the number of recovery containers 13 can be reduced.

The fourth pressure sensor 24 is provided at the permeation side of the third membrane 9, and controls the output of the fourth pressure sensor 24 to constantly show a predetermined fixed pressure with stability. Thus, an expensive concentration analyzer 53 becomes unnecessary. As a result, costs can be reduced in the above-noted embodiment and examples 1 to 3. Furthermore, since the fourth pressure sensor 24 has a continuous output, it can easily respond to a change in the state of the exhaust gas. Thus, control precision improves, and recovery concentration becomes stable (see the solid line in FIG. 4).

On the other hand, when the internal pressure of the first tank 3 is controlled to be constant, the opening of the fourth control valve 21 is controlled without taking in outside air from the first line 15. At the same time, the opening of the needle valve 23 of the third line 22 is adjusted, and a portion of the first permeable gas flow is taken in from the third line 22, Thus, as the exhaust gas is not diluted, the recovery efficiency of PFC improves.

Moreover, when the internal pressure of the first tank 3 is controlled to be constant as described above, outside air is not taken in, unlike the conventional art shown in FIG. 8, so that the control range of internal pressure of the first tank 3 is not reduced. Thus, even if the state of 21 the exhaust gas changes, this embodiment can easily respond to the change. The internal pressure of the first tank 3 can be controlled to be constant. Additionally, as described above, outside air is not taken in, and the control range of internal pressure of the first tank 3 is not reduced, so that there is no need to increase the level of negative pressure of the first tank 3. Thus, it is possible to reduce the load of the compressor 4 which high-pressurizes a gas flow from the first tank 3, and the running cost of the compressor 4 can be reduced. Moreover, the first tank 3 and the second tank 5 can function as a buffer to provide constant pressure.

Moreover, as described above, even if the state of the exhaust gas changes, the embodiment can easily respond to the change and can control the internal pressure of the first tank 3 to be constant. Thus, in the PFC separation recovery method in which the fourth pressure sensor 24 is provided on the third permeable gas flow and the downstream is connected to the third tank 3, the fourth pressure sensor 24 can be controlled to show an accurate predetermined fixed pressure even if the state of the exhaust gas changes.

Furthermore, as described above, even when the state of the exhaust gas changes, the internal pressure of the first tank 3 can be controlled to be constant. Thus, pressure on the upstream side of the blower 2 (output of the first pressure sensor 14) can be controlled to accurate target pressure by the control of the blower 2 using the inverter 2a.

Additionally, as described above, the internal pressure of the first tank 3 can be controlled to be constant even if the state of the exhaust gas changes. Thus, even if the number of membranes used to separate the permeation side from the non-permeation side increases and the number of processes to return the gas on the permeation side to the first tank 3 for circulation is increased, the embodiment can respond thereto. Increasing the number of gas flows on the permeation side for circulation improves the recovery efficiency of the PFC gas.

Moreover, although the fourth pressure sensor 24 was provided in the embodiment above, the sensor may be provided on the permeation side of the second membrane 8 or on the permeation side after the fourth membrane (not shown in the figure) by increasing the number of membranes. It is also most preferable to provide this sensor on the permeation side of the last membrane. Moreover, instead of the fourth pressure sensor 24, a flow sensor, not affected by PFC gas concentration, may be used to detect a flow rate on the permeation side of the third membrane 9 and to control the flow rate constant.

Moreover, in the embodiment mentioned above,-diluent gas (N2 gas or the like), which hardly contains PFC gas, can be recovered from the exhaust gas by recovering gas released from the fourth control valve 21. In the above-noted embodiment, the arrangement of the fourth control valve 21 and the needle valve 23 of the third line 22 may be reversed. Furthermore, a control valve, instead of the needle valve 23, may be provided to improve control precision by controlling the control valve and the fourth control valve 21.

Moreover, although three membranes are used and three valves are used on the non-permeation side of the third membrane 9, these numbers are not particularly limited.

INDUSTRIAL APPLICABILITY

As described above, the perfluoro compound separation recovery method of the present invention separates and recovers perfluoro compound gas by contacting it with a membrane which permeates more diluent gas than perfluoro compound gas, after the pressure of diluted mixed gas consisting of perfluoro compound gas and diluent gas is raised to a high level. The method includes the steps of separating diluted mixed gas into a permeable gas flow rich in diluent gas and a non-permeable gas flow rich in perfluoro compound gas by contacting high-pressurized diluted mixed gas with the above-mentioned membrane; repeatedly separating the non-permeable gas flow into another permeable gas flow and another non-permeable gas flow by contacting it with another membrane having the same functions as those of the membrane mentioned above; detecting the pressure or flow rate of the other permeable gas flow; and controlling the flow rate of the other non-permeable gas flow so as to set the pressure or flow rate constant. Thus, even if the concentration of PFC gas in the diluted mixed gas changes, the concentration can be kept roughly the same after the treatment.

Moreover, when the perfluoro compound separation recovery method of the present invention includes a step of controlling pre-pressurized diluted mixed gas at a predetermined fixed pressure by returning an appropriate amount of the permeable gas flow into the pre-pressurized diluted mixed gas, and when the above control in this step is carried out without taking in outside air, the recovery efficiency of PFC improves as diluted mixed gas is not diluted with outside air. Additionally, since outside air is not taken in when the pre-pressurized diluted mixed gas is controlled at the fixed pressure as described above, the control range of pressure of the pre-pressurized diluted mixed gas is not reduced. Thus, even if the state of the diluted mixed gas changes, the method can easily respond to the change. Moreover, as outside air is not taken in as described above, the load can be kept small when the pressure of the diluted mixed gas is raised to a high level.

The perfluoro compound separation recovery system of the present invention has a means to raise the pressure of diluted mixed gas consisting of perfluoro compound gas and diluent gas; and a membrane to separate high-pressurized diluted mixed gas into a permeable gas flow rich in diluent gas and a non-permeable gas flow rich in perfluoro compound gas. The system includes another membrane to separate the above-noted non-permeable gas flow into another permeable gas flow and another non-permeable gas flow; a means to detect the pressure or flow rate of the other permeable gas flow; and a means to control the flow rate of the other non-permeable gas flow. Thus, an expensive concentration analyzer becomes unnecessary, and the cost can be reduced. Furthermore, as the pressure or flow rates can be continuously detected, the system can respond to the periodic change in the state of the exhaust gas, and the concentration of PFC gas after the treatment can be kept roughly the same.

What is claimed is:

1. A perfluoro compound separation recovery method for separating and recovering perfluoro compound gas by contacting it with a membrane which permeates more diluent gas than perfluoro compound gas, after high-pressurizing diluted mixed gas consisting of perfluoro compound gas and diluent gas, comprising the steps of separating high-pressurized diluted mixed gas into a permeable gas flow rich in diluent gas and a non-permeable gas flow rich in perfluoro compound gas by contacting it to the membrane; repeatedly separating the non-permeable gas flow into another permeable gas flow and another non-permeable gas flow by contacting the non-permeable gas flow with another membrane having the same functions as those of the membrane; detecting pressure or a flow rate of the other permeable gas flow; controlling a flow rate of the other non-permeable gas flow so as to set the pressure or flow rate constant; and recovering the other non-permeable gas flow.

2. The perfluoro compound separation recovery method according to claim 1, comprising the step of controlling pre-pressurized diluted mixed gas at predetermined fixed pressure by returning an appropriate amount of the permeable gas flow into the pre-pressurized diluted mixed gas; wherein the control is performed without taking in outside air in the step.

3. The perfluoro compound separation recovery method according to claim 2, wherein one or more of the other membranes is connected in series; another non-permeable gas flow which was separated at each membrane, except for the last other membrane, is sequentially contacted with the following other membranes; either pressure or a flow rate of another permeable gas flow which was separated at the other membrane, is detected; a flow rate of another non-permeable gas flow that was separated at the other membrane is controlled so as to make the pressure or flow rate constant; and the last other non-permeable gas flow that was separated at the last membrane, is recovered.

4. The perfluoro compound separation recovery method according to claim 1, wherein one or more of the other membranes is connected in series; another non-permeable gas flow which was separated at each membrane, except for the last other membrane, is sequentially contacted with the following other membranes; either pressure or a flow rate of another permeable gas flow which was separated at the other membrane, is detected; a flow rate of another non-permeable gas flow that was separated at the other membrane is controlled so as to make the pressure or flow rate constant; and the last other non-permeable gas flow that was separated at the last membrane, is recovered.

5. A perfluoro compound separation recovery system including a means to raise pressure of diluted mixed gas consisting of perfluoro compound gas and diluent gas, and a membrane to separate high-pressurized diluted mixed gas into a permeable gas flow rich in diluent gas and a non-permeable gas flow rich in perfluoro compound gas; comprising another membrane to separate the non-permeable gas flow into another permeable gas flow and another non-permeable gas flow; a means to detect pressure or a flow rate of the other permeable gas flow; a means to control a flow rate of the other non-permeable gas flow; and a means to recover the other non-permeable gas flow.

6. The perfluoro compound separation recovery system according to claim 5, comprising a means to return an appropriate amount of the permeable gas flow into the pre-pressurized diluted mixed gas; and a means to control the pre-pressurized diluted mixed gas at predetermined fixed pressure.

7. The perfluoro compound separation recovery system according to claim 6, comprising a means to detect either pressure or a flow rate of another permeable gas flow that was separated by the other membrane, by connecting one or more of the other membranes in series and sequentially contacting another non-permeable gas flow that was separated at each membrane, except for the last other membrane, to the following other membrane; a means to control a flow rate of another non-permeable. gas flow that was separated at the other membrane; and a means to recover the last other non-permeable gas flow that was separated at the last membrane.

8. The perfluoro compound separation recovery system according to claim 5, comprising a means to detect either pressure or a flow rate of another permeable gas flow that was separated by the other membrane, by connecting one or more of the other membranes in series and sequentially contacting another non-permeable gas flow that was separated at each membrane, except for the last other membrane, to the following other membrane; a means to control a flow rate of another non-permeable gas flow that was separated at the other membrane; and a means to recover the last other non-permeable gas flow that was separated at the last membrane.

* * * * *